United States Patent [19]

Green et al.

[11] Patent Number: 5,691,487

[45] Date of Patent: Nov. 25, 1997

[54] COUPLING OF AIR SAMPLES TO A SAMPLER

[75] Inventors: Thomas B. Green, Batavia, Ohio; Todd A. Wolsing, Taylor Mill, Ky.; Joseph A. Borer, Cincinnati, Ohio

[73] Assignee: Tekmar Company, Cincinnati, Ohio

[21] Appl. No.: 556,666

[22] Filed: Nov. 13, 1995

[51] Int. Cl.[6] .............................. G01N 1/22; G01N 1/26
[52] U.S. Cl. ............................ 73/863.86; 73/863.31; 73/864.91
[58] Field of Search ........................ 73/863.86, 863.31, 73/863.33, 864.51, 864.91, 864.63, 864, 863.71, 863.72

[56] References Cited

U.S. PATENT DOCUMENTS

| | | | |
|---|---|---|---|
| 3,731,539 | 5/1973 | Brittan et al. | 73/863.31 X |
| 4,454,773 | 6/1984 | Brunner et al. | 73/863.86 X |
| 4,704,910 | 11/1987 | Conrad | 73/863.21 |
| 5,192,200 | 3/1993 | Lilie et al. | 137/855 X |
| 5,240,681 | 8/1993 | O'Lear et al. | 73/864.81 X |
| 5,321,984 | 6/1994 | Stroupe | 73/863.11 |
| 5,410,918 | 5/1995 | Zimmerman | 73/863.31 X |
| 5,417,314 | 5/1995 | Sproston et al. | 137/909 X |

OTHER PUBLICATIONS

"Programmable Gls Sample Selector" *Kent Tech. Rev. (GB)*, No. 25, Jul. 1979 pp. 10–13 in 73/863.33.
Tekmar ALS 2016/ALS 2032—User Manual, Jan. 31, 1994, cover, guide page, pp. i–iv, 1–79, 10 pages drawings, 3 pages index.

*Primary Examiner*—Thomas P. Noland
*Attorney, Agent, or Firm*—Westman, Champlin & Kelly, P.A.

[57] ABSTRACT

An air sampler includes a stand for supporting a plurality of sample enclosures from which samples can be randomly and selectively obtained. In a first embodiment, a bracket adjustably fixed to the stand supports each of the sample enclosures. In a second embodiment, an inlet line fluidly couples each of the sample enclosures to a valve carried by the stand. The inlet line has a flexible portion adjacent the end coupleable to the sample enclosure to allow limited misalignment between the sample enclosure and the stand.

12 Claims, 5 Drawing Sheets

COUPLING OF AIR SAMPLES TO A SAMPLER

BACKGROUND OF THE INVENTION

The present invention relates to analytical apparatuses for measuring selected compounds in air samples. More particularly, the present invention relates to a bracket assembly and coupling device for supporting and coupling a sample enclosure to an air sampler.

Samplers for sampling air samples collected in pre-evacuated SUMMA canisters are known. The canisters used for sampling atmospheric gases are generally made of stainless steel and have a volume of six (6) or fifteen (15) liters at atmospheric pressure. Each canister is typically spherical in shape, and is supplied with a stand so that it may be placed on a flat surface. Guard plates are attached to an outer surface of the canister and are positioned on opposite sides of a connector valve. Arcuate members join the guard plates together and form apertures with the guard plates so as to provide handles for each canister.

The sampler preferably supports a plurality of canisters so that random, controlled access of the contents of the canisters can be made. U.S. Pat. No. 5,321,984 discloses a cart having shelf members for holding a plurality of canisters. Each canister couples to a fitting on one end of a sample inlet line. The opposite end of each sample inlet line is coupled to an electrically actuated multiposition valve.

SUMMARY OF THE INVENTION

The present invention is an air sampler capable of supporting sample enclosures and obtaining samples therefrom. As used herein, the term "sample enclosure" includes any standard gas collection device such as standard stainless steel canisters (e.g. SUMMA), bags (e.g. TEDLAR), glass bottles and the like which may be supported by the present invention.

In one broad aspect of the present invention, the air sampler includes a stand and a bracket adjustably fixed to the stand for supporting a sample enclosure. A valve having an inlet and an outlet and carried by the stand controls samples taken from the sample enclosure. An inlet line transfers samples from the sample enclosure to the valve. The inlet line has a first end coupleable to the sample enclosure and a second end fluidly coupled to the valve.

In another broad aspect of the invention, the air sampler includes a stand adapted to support a sample enclosure. A valve having an inlet and an outlet and carried by the stand controls samples taken from the sample enclosure. An inlet line transfers samples from the sample enclosure to the valve. The inlet line has a first end, which is coupleable to the sample enclosure, and a second end fluidly coupled to the valve. The inlet line further includes a flexible portion, preferably adjacent the first end, so as to allow the inlet line to flex and accommodate any misalignment present in the position of the sample enclosure.

DETAILED DESCRIPTION OF THE PREFERRED EMBODIMENTS

Figure 1:
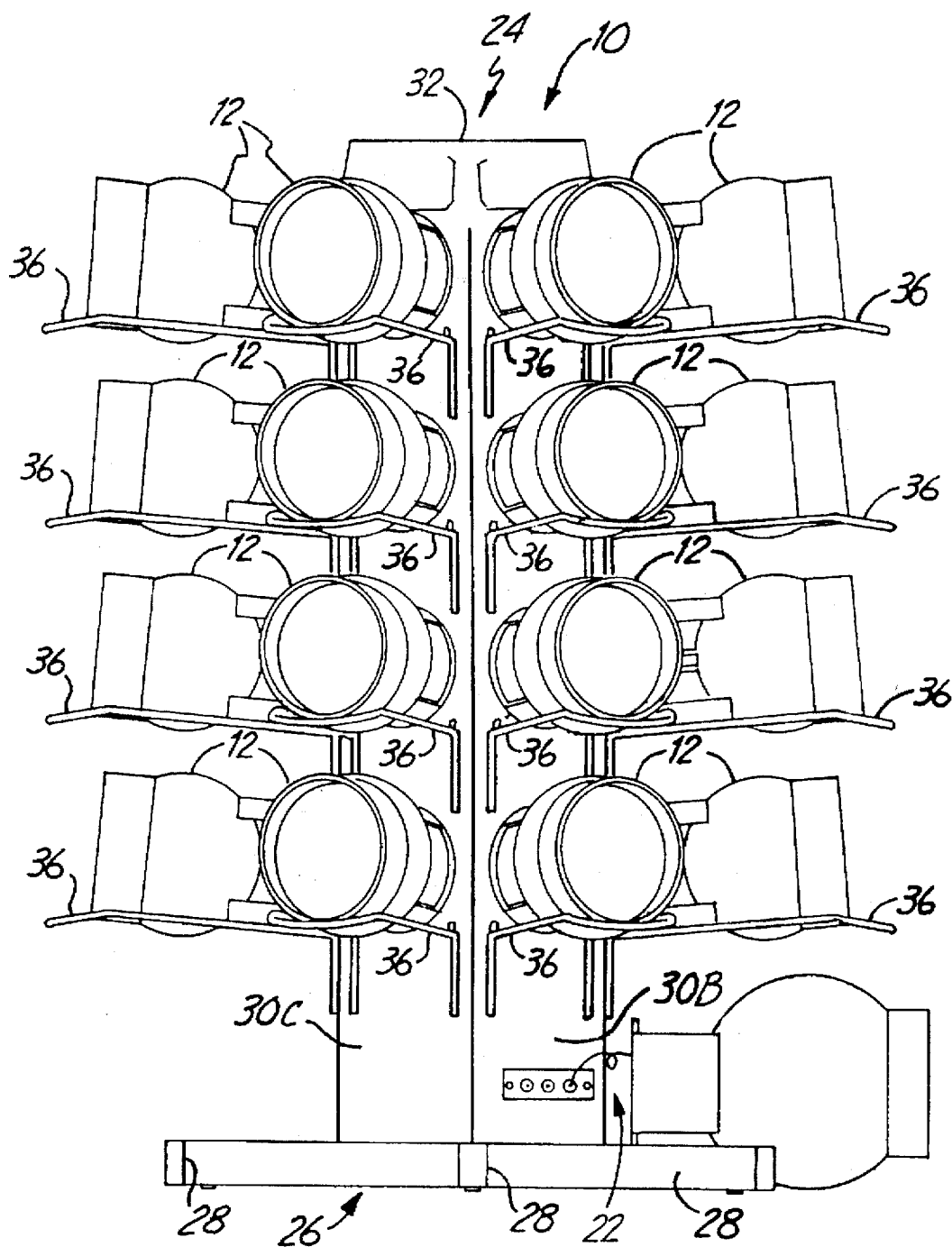
FIG. 1 is a front elevational view of an air sampler of the present invention.
Figure 2:
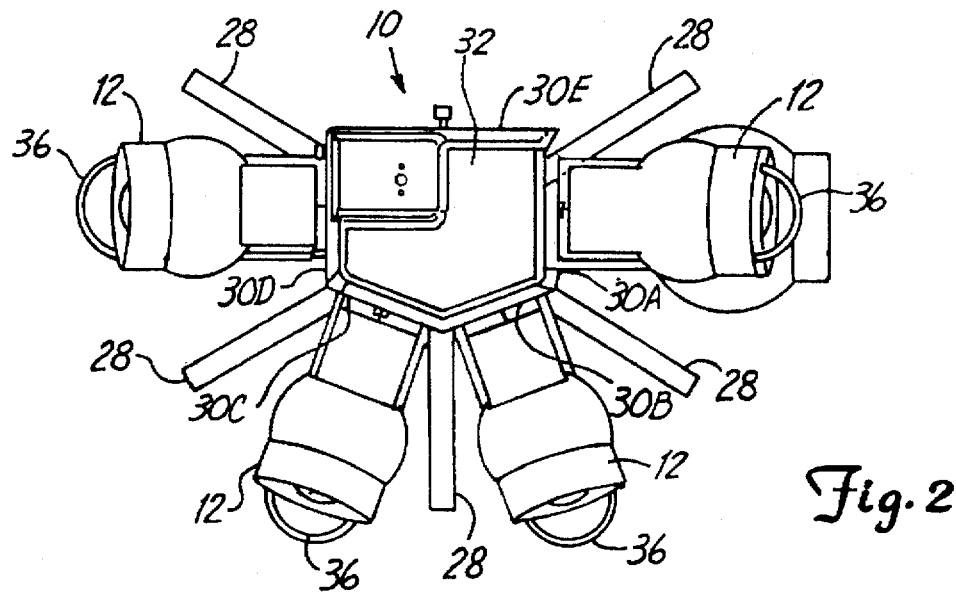
FIG. 2 is a top plan view of the air sampler of FIG. 1.
Figure 3:
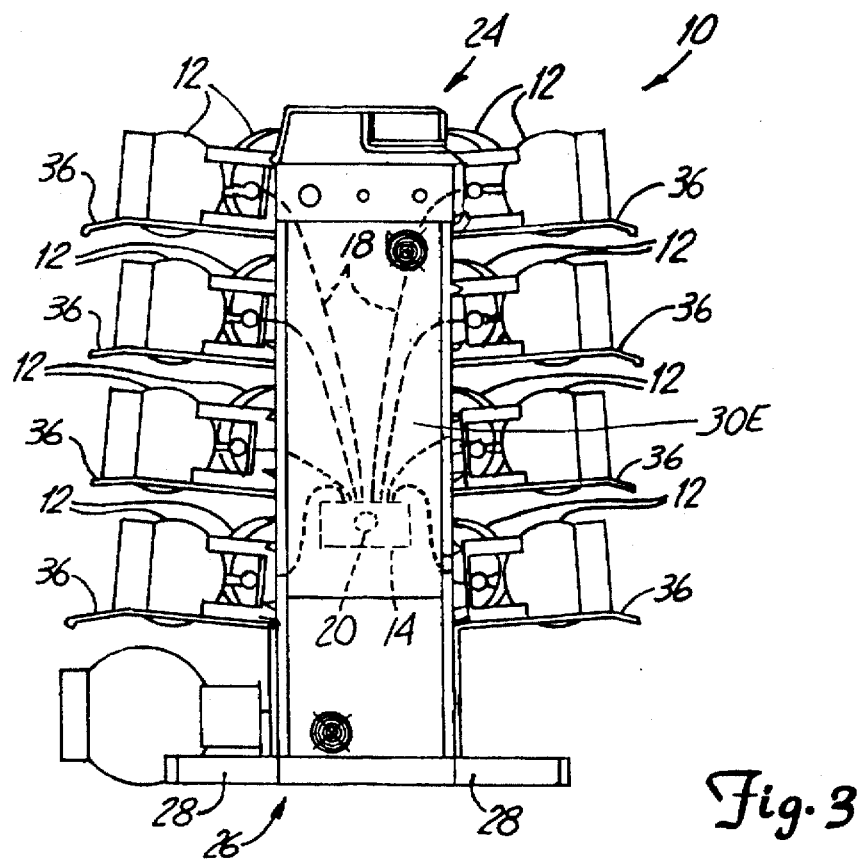
FIG. 3 is a rear elevational view of the air sampler of FIG. 1 with some components illustrated with dashed lines.

FIGS. 1–3 illustrate an air sampler of the present invention generally at 10. The air sampler 10 supports a plurality of sample enclosures, herein depicted as canisters 12, which are used for holding air samples taken at remote locations. The air sampler 10 allows random, controlled access of the contents of the canisters 12 so that samples may be selectively removed from the canisters 12, as needed.

A multiposition valve 14 illustrated with dashed lines in FIG. 3 controls access to each of the canisters 12. Separate inlet lines 18 having, preferably, valve couplers 22 (FIG. 6), described below, couple each of the canisters 12 to an inlet port of the valve 14. The multiposition valve 14 transfers contents of the canisters 12 to an outlet port 20. The outlet port 20 can be coupled to an external line extending out of the air sampler 10 which, in turn, can be coupled to other known analytical instruments such as a gas chromatograph. In another embodiment, the outlet port 20 can be coupled to other devices in the air sampler 10 to further prepare the sample taken from the selected canister as described in co-pending application entitled AIR SAMPLER WITH TRAP, Ser. No. 08/556,620, filed on the same date as the present application and incorporated herein by reference.

The air sampler 10 includes a stand 24 having a base 26 formed of radially extending legs 28. Side panels 30A, 30B, 30C and 30D extend upwardly from the base 26 and with a cover 32 form part of an enclosure for components mounted inside the stand 24 such as the multiposition valve 14. A hinged door 30E serves both as a rear panel and as an access to the valve 14 and other internal components.

A plurality of support brackets 36 are mounted on each of the side panels 30A–30D. The support brackets 36 are spaced vertically, a sufficient distance apart from each other, so that canisters 12 can pass between the support brackets 36 on which they are to rest and any support brackets 36 located above. The side panels 30A–30D are of sufficient width so that the canisters 12 do not come into contact with each other. In the embodiment illustrated, each side panel 30A–30D carries four canisters 12 for a total capacity of sixteen (16) canisters 12. The various components of the stand 24 can be made of any material known in the art which is sufficiently strong enough to hold the canisters 12, for example, metal, wood, plastics, manufactured composite materials, and combinations thereof.

Figure 4:
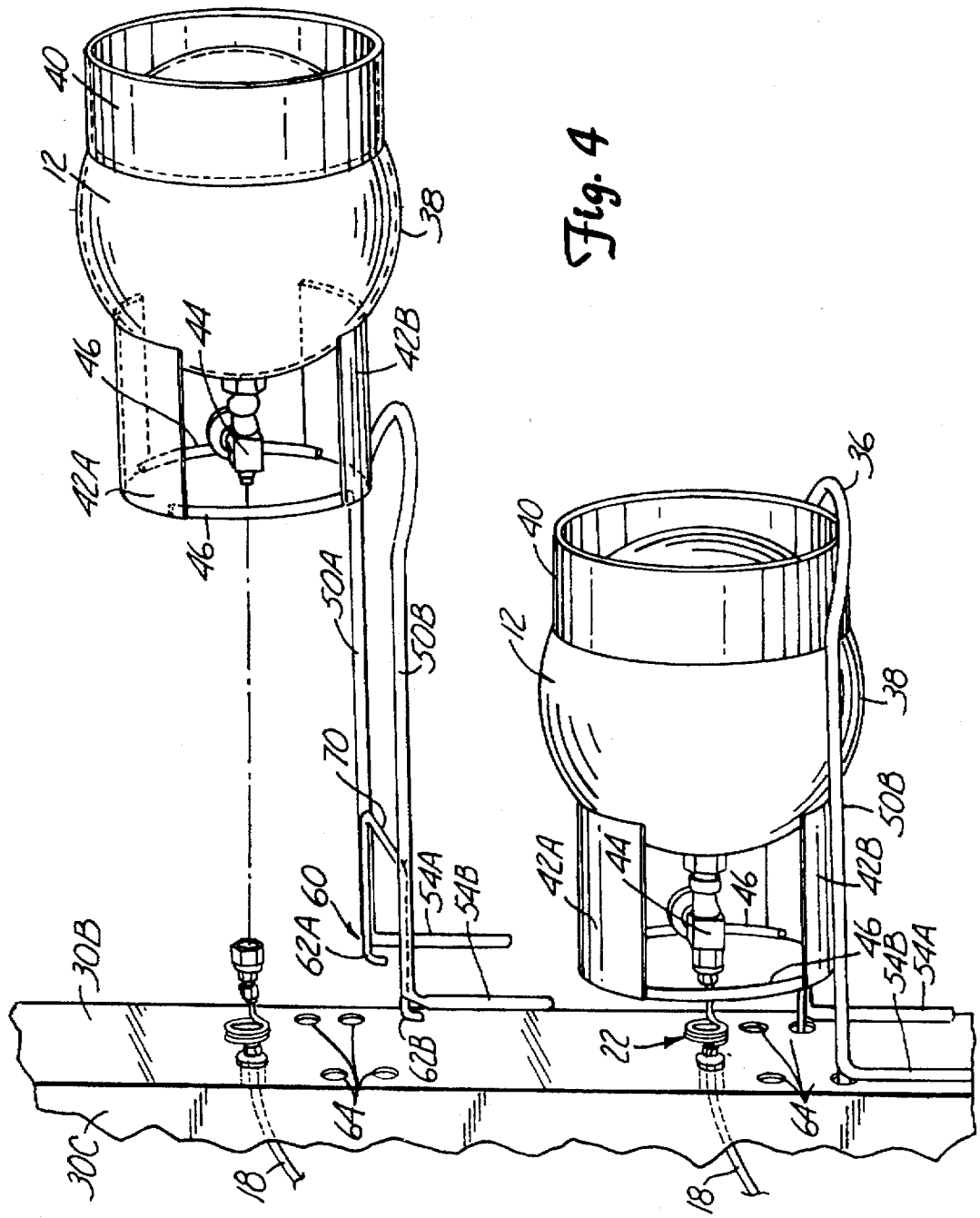
FIG. 4 is a portion of a side panel with a support bracket mounted to the side panel and a sample enclosure coupled to a flexible inlet line coupler, and a second support bracket and second sample enclosure separated from the side panel.

FIG. 4 illustrates a portion of side panel 30B. Preferably, each of support brackets 36 are adjustably secured to each corresponding side panel 30A–30D so as to accommodate canisters 12 of different sizes. In the embodiment illustrated, each canister 12 includes a spherical body 38 and a stand 40. The stand 40 supports the canister 12 when the canister 12 is placed on a flat surface. Guard plates 42A and 42B extend away from the body 38 to protect a valve 44. Arcuate members 46 join the guard plates 42A and 42B together. The canisters 12 are manufactured in selected standard sizes, for example, six (6) and fifteen (15) liter capacities at atmospheric pressures. The adjustable support brackets 36 allow canisters 12 of different size to be properly positioned on the stand 24 so that the valves 44 at least roughly are aligned with the inlet couplers 22.

Figure 5:
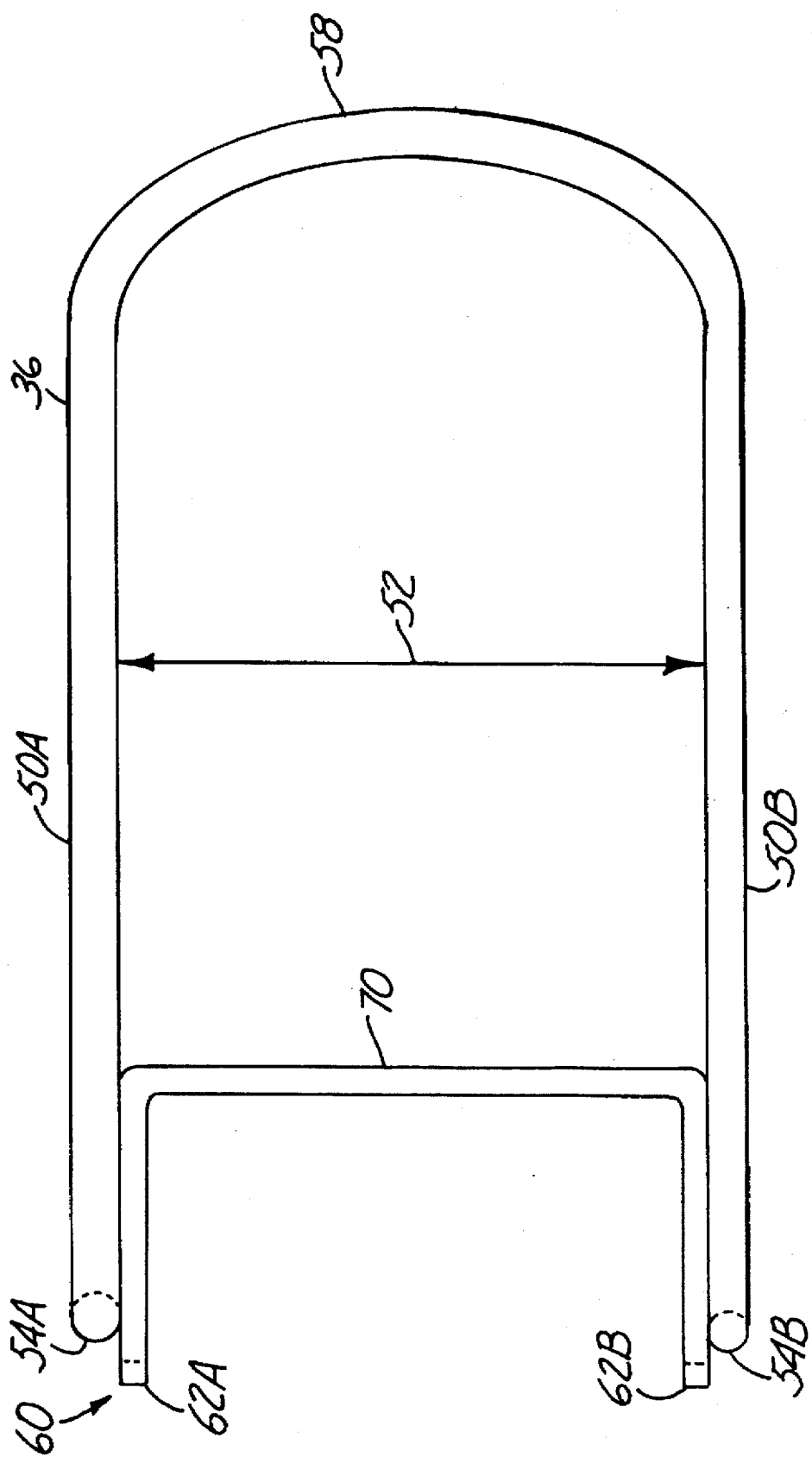
FIG. 5 is a top plan view of a support bracket.

Referring to FIG. 5, each of the brackets 36 include spaced-apart rod portions 50A and 50B having a width 52 less than a diameter of the body portion 38 of the smallest canister 12 to be supported. Downwardly extending portions 54A and 54B are joined to the rod portions 50A and 50B, respectively. As illustrated in FIG. 4, the downwardly extending portions 54A and 54B contact the side panel 30B to provide support. At an end opposite portions 54A and 54B, the rod portions 50A and 50B are joined together with an arcuate member 58 that tilts downwardly with respect to the rod portions 50A and 50B. Preferably, portions 50A, 50B, 54A, 54B and arcuate member 58 are integrally formed together as a single unitary piece.

A coupling device 60 engages the side panel 30B to hold the support bracket 36 in proper position. In the embodiment illustrated, the coupling device 60 includes a pair of "L-shaped" posts 62A and 62B that can extend through mounting apertures 64 located in each of side panels 30A–30D. Referring to FIG. 4, preferably, the mounting apertures 64 are organized in vertically spaced-apart pairs at varying distances from the corresponding inlet coupler 22. The mounting apertures 64 are preferably elongated so as to accept the downwardly extending portions of each of the posts 62A and 62B. After the posts 62A and 62B have been inserted through a selected pair of apertures 64, the support bracket 36 is pushed downwardly so that portions of the side panel 30B are located between opposed facing surfaces of the posts 62A–62B and the downwardly extending portions 54A–54B.

The rod portions 50A and 50B guide the canister 12 so that the valve 44 is proximate to the inlet coupler 22. A support rod 70, preferably integrally formed with the posts 62A and 62B, extends between the rod portions 50A and 50B to further support the canister 12 by contacting the guard plate 42B.

Figure 6:
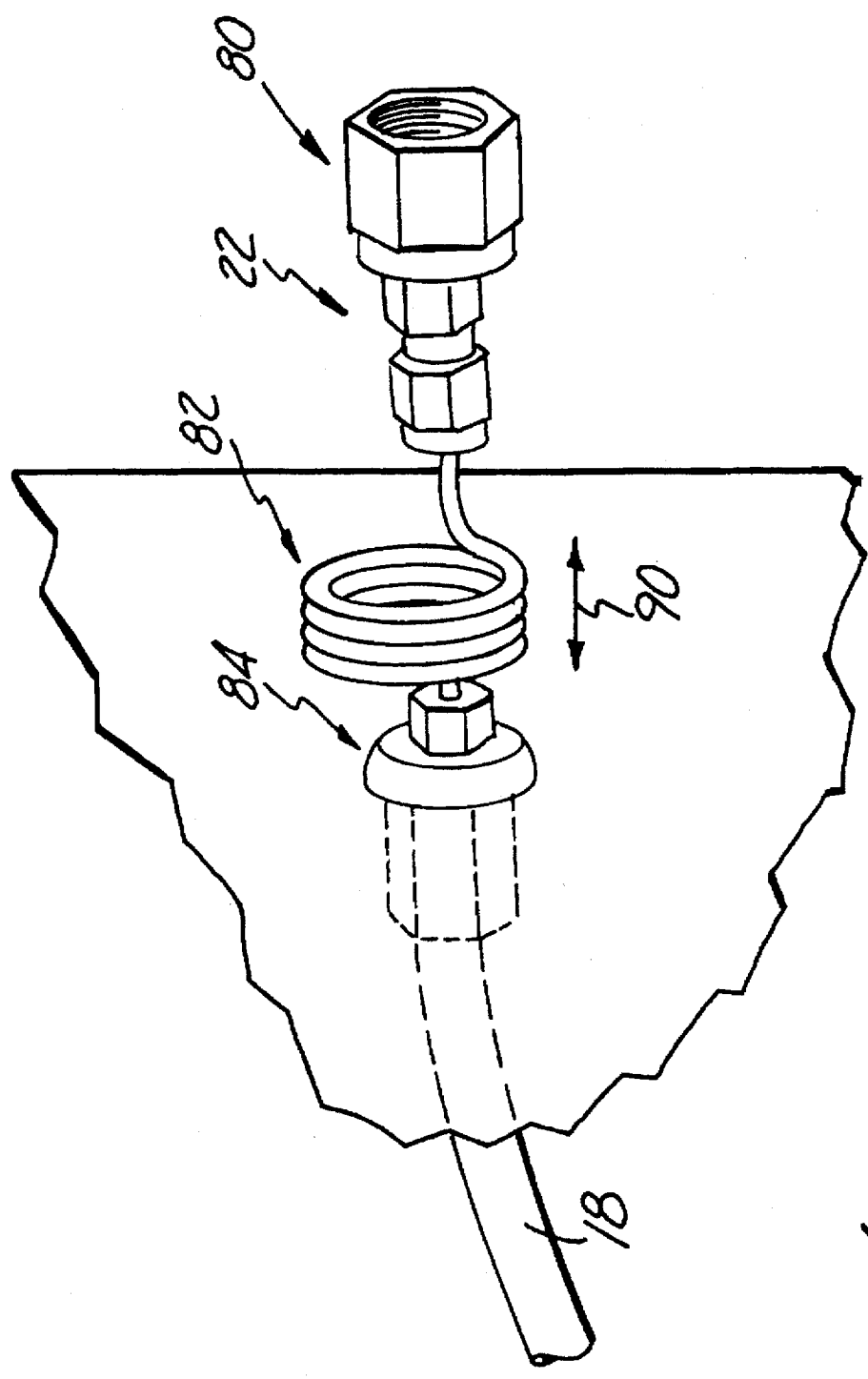
FIG. 6 is an enlarged perspective view of the flexible inlet line coupler.

An enlarged detailed view of the inlet coupler 22 is illustrated in FIG. 6. The inlet coupler 22 includes a suitable fitting 80 allowing it to be fluidly coupled to the valve 44 of a given canister 12. A flexible tube 82 couples the fitting 80 to a mounting fitting 84 secured to each side panel 30A–30D. The flexible tube 82 allows the fitting 80 to move relative to the mounting fitting 84. Movement of the fitting 80 adjusts for any misalignment between the canister 12 and the support bracket 36 upon which it rests. Preferably, the flexible portion 82 comprises a coiled tube wherein expansion, contraction, and bending of the coil allows the fitting 80 to move relative to the mounting fitting 84. Preferably, the flexible tube 82 can expand and contract in the direction indicated by double arrow 90. Although the flexible tube 82 can be formed of any suitable material such as metal, plastic, or Teflon™, in a preferred embodiment, the flexible tube 82 is made of Polyetheretherketone. Polyetheretherketone is preferred because it is less permeable than Teflon™ is not as susceptible to fatigue or cracking as found with metal tubing.

Although the present invention has been described with reference to preferred embodiments, workers skilled in the art will recognize that changes may be made in form and detail without departing from the spirit and scope of the invention.

What is claimed is:

1. An air sampler, comprising:
   a stand;
   a bracket adjustably fixed to the stand for supporting a sample enclosure, wherein the bracket is adjustable between a first position to support a relatively small sample enclosure and a second position to support a relatively large sample enclosure;
   a valve carried by the stand for controlling samples taken from the sample enclosure, the valve having an inlet and an outlet; and
   an inlet line having a first end coupleable to the sample enclosure and a second end fluidly coupled to the valve.

2. The air sampler of claim 1 wherein the stand includes a plurality of mounting apertures and the bracket includes posts insertable in selected apertures of the plurality of mounting apertures.

3. The air sampler of claim 2 wherein the bracket includes an aperture adapted to receive a portion of the sample enclosure.

4. The air sampler of claim 1 wherein the inlet line includes a flexible portion adjacent the first end.

5. The air sampler of claim 4 wherein the flexible portion is disposed on an exterior side of the stand.

6. The air sampler of claim 5 wherein the flexible portion comprises a tube forming a coil.

7. The air sampler of claim 1, wherein the stand has a first and second pair of apertures, and wherein the bracket mates with the first pair of apertures in the first position and mates with the second pair of apertures in the second position.

8. An air sampler, comprising:
   a stand having a plurality of mounting apertures;
   a bracket adjustably fixed to the stand for supporting a sample enclosure, the bracket having posts insertable in selected apertures of the plurality of mounting apertures;
   a valve carried by the stand for controlling samples taken from the sample enclosure, the valve having an inlet and an outlet; and
   an inlet line having a first end coupleable to the sample enclosure and a second end fluidly coupled to the valve.

9. The air sampler of claim 8 and wherein the inlet line includes a flexible portion adjacent the first end.

10. An air sampler, comprising:
    a stand having a plurality of side panels, each side panel having a plurality of mounting apertures;
    a plurality of brackets adjustably fixed to the stand, wherein each bracket is capable of supporting a sample enclosure and each bracket includes a post insertable in selected apertures of the plurality of mounting apertures;
    a valve carried by the stand for controlling samples taken from the sample enclosures, the valve having an inlet portion and an outlet portion; and
    a plurality of inlet lines, wherein each inlet line has a first end coupleable to a sample enclosure and a second end fluidly coupled to the inlet portion of the valve.

11. The air sampler of claim 10, wherein each bracket is adjustable between a first position to support a relatively small sample enclosure and a second position to support a relatively large sample enclosure.

12. The air sampler of claim 10 wherein the side panels are vertical and the plurality of mounting apertures are vertically spaced on the side panels.

* * * * *

UNITED STATES PATENT AND TRADEMARK OFFICE
CERTIFICATE OF CORRECTION

PATENT NO. : 5,691,487
DATED : November 25, 1997
INVENTOR(S) : Green et al.

It is certified that error appears in the above-indentified patent and that said Letters Patent is hereby corrected as shown below:

ON THE TITLE PAGE:

Item [56] References Cited

OTHER PUBLICATIONS

Line 1, replace "Gls" with --Gas--.

Signed and Sealed this

Ninth Day of June, 1998

*Attest:*

BRUCE LEHMAN

*Attesting Officer*      *Commissioner of Patents and Trademarks*